United States Patent
Matsunaga et al.

(10) Patent No.: US 12,390,345 B2
(45) Date of Patent: Aug. 19, 2025

(54) SPINAL IMPLANT AND METHOD OF MANUFACTURING SPINAL IMPLANT

(71) Applicants: KYOCERA CORPORATION, Kyoto (JP); SAGA UNIVERSITY, Saga (JP)

(72) Inventors: Kazuya Matsunaga, Kyoto (JP); Fumiya Nakada, Kyoto (JP); Masaaki Mawatari, Saga (JP); Tadatsugu Morimoto, Saga (JP)

(73) Assignees: KYOCERA Corporation, Kyoto (JP); SAGA University, Saga (JP)

( * ) Notice: Subject to any disclaimer, the term of this patent is extended or adjusted under 35 U.S.C. 154(b) by 290 days.

(21) Appl. No.: 17/795,821

(22) PCT Filed: Feb. 1, 2021

(86) PCT No.: PCT/JP2021/003452
§ 371 (c)(1),
(2) Date: Jul. 27, 2022

(87) PCT Pub. No.: WO2021/153795
PCT Pub. Date: Aug. 5, 2021

(65) Prior Publication Data
US 2023/0076858 A1     Mar. 9, 2023

(30) Foreign Application Priority Data

Jan. 31, 2020  (JP) ................... 2020-015252
Jan. 31, 2020  (JP) ................... 2020-015253

(51) Int. Cl.
*A61F 2/44*   (2006.01)
*A61F 2/30*   (2006.01)

(52) U.S. Cl.
CPC ...... *A61F 2/447* (2013.01); *A61F 2002/3006* (2013.01); *A61F 2002/30774* (2013.01); *A61F 2002/30904* (2013.01); *A61F 2002/448* (2013.01)

(58) Field of Classification Search
CPC ........ A61F 2/44–447; A61F 2002/3006; A61F 2002/30774; A61F 2002/30904; A61F 2002/448
See application file for complete search history.

(56) References Cited

U.S. PATENT DOCUMENTS

| | | |
|---|---|---|
| 2002/0004683 A1 * | 1/2002 | Michelson ............ A61F 2/4637 623/17.16 |
| 2003/0023306 A1 | 1/2003 | Liu |
| 2006/0282166 A1 | 12/2006 | Molz |
| 2007/0118220 A1 | 5/2007 | Liu |
| 2009/0280156 A1 | 11/2009 | Hotokebuchi |

(Continued)

FOREIGN PATENT DOCUMENTS

| | | |
|---|---|---|
| AU | 2019219236 A1 | 9/2020 |
| JP | H02241461 A | 9/1990 |

(Continued)

*Primary Examiner* — Nicholas J Plionis
(74) *Attorney, Agent, or Firm* — Procopio, Cory, Hargreaves & Savtich LLP

(57) ABSTRACT

A spinal implant includes a base and a coating film disposed on the base and including a calcium phosphate-based material and an antimicrobial agent. A surface of the base includes a first region in which the coating film is disposed and a second region exposed from the coating film.

16 Claims, 3 Drawing Sheets

(56) References Cited

U.S. PATENT DOCUMENTS

| | | |
|---|---|---|
| 2010/0114105 A1 | 5/2010 | Butters et al. |
| 2010/0228296 A1* | 9/2010 | Vraney ................ A61F 2/447 |
| | | 606/279 |
| 2011/0008407 A1 | 1/2011 | Gan |
| 2011/0190888 A1* | 8/2011 | Bertele ................ A61F 2/447 |
| | | 623/17.11 |
| 2011/0264152 A1* | 10/2011 | Weiman ............ A61B 17/1757 |
| | | 606/86 R |
| 2013/0116790 A1 | 5/2013 | Seifert |
| 2013/0138223 A1* | 5/2013 | Mawatari ............ A61L 27/32 |
| | | 623/23.61 |
| 2014/0228958 A1 | 8/2014 | Niemiec |
| 2014/0287018 A1 | 9/2014 | Soo et al. |
| 2015/0018965 A1 | 1/2015 | Mawatari |
| 2015/0056264 A1 | 2/2015 | Gan |
| 2016/0058568 A1 | 3/2016 | Bagga |
| 2017/0119932 A1 | 5/2017 | Mawatari |
| 2017/0348114 A1 | 12/2017 | Jones et al. |
| 2018/0192939 A1 | 7/2018 | Roth |
| 2018/0303629 A1* | 10/2018 | Lauf ...................... A61B 17/70 |
| 2018/0361022 A1 | 12/2018 | Hotokebuchi |
| 2019/0254840 A1 | 8/2019 | Gray |
| 2019/0290361 A1 | 9/2019 | Shalayev |
| 2020/0215230 A1 | 7/2020 | Hotokebuchi |
| 2021/0052780 A1 | 2/2021 | Mawatari |

FOREIGN PATENT DOCUMENTS

| | | |
|---|---|---|
| JP | H10155822 A | 6/1998 |
| JP | 2003-526458 A | 9/2003 |
| JP | 2008-073098 A1 | 4/2008 |
| JP | 2011-512959 A | 4/2011 |
| JP | 2011234924 A | 11/2011 |
| JP | 2012-040194 A | 3/2012 |
| JP | 2013-518619 A | 5/2013 |
| JP | 2014-533178 A | 12/2014 |
| WO | 2013114947 A | 8/2013 |
| WO | 2019155021 A | 8/2019 |

\* cited by examiner

SPINAL IMPLANT AND METHOD OF MANUFACTURING SPINAL IMPLANT

TECHNICAL FIELD

The present disclosure relates to a spinal implant that is inserted between adjacent vertebrae to replace or supplement an intervertebral disk.

BACKGROUND ART

Conventionally, there is known a spinal implant for replacing or supplementing an intervertebral disk removed in a surgery operation or the like to correct degenerative or diseased conditions such as hernias. For example, Patent Document 1 describes a vertebral implant including land portions and grooves on a top surface and a bottom surface of a main body.

Further, Patent Document 2 describes a coating for a medical implant, wherein a part of the coating includes a bone-binding agent and a part of the coating includes an antimicrobial metal agent including silver. Furthermore, Patent Documents 3 and 4 describe a bioimplant on which a coating film made of a calcium phosphate-based material is formed.

CITATION LIST

Patent Literature

Patent Document 1: JP 2003-526458 T
Patent Document 2: JP 2011-512959 T
Patent Document 3: JP 2008-73098 A
Patent Document 4: WO 2013/114947

SUMMARY

A spinal implant according to an aspect of the present disclosure includes a base and a coating film disposed on the base and including a calcium phosphate-based material and an antimicrobial agent, in which a surface of the base includes a first region and a second region, the first region being disposed with the coating film, and the second region being exposed from the coating film.

A spinal implant according to an aspect of the present disclosure includes a base and a coating film disposed on the base and including a calcium phosphate-based material and an antimicrobial agent, in which the coating film includes a first region and a sixth region having a smaller film thickness than the first region.

A method of manufacturing a spinal implant according to an aspect of the present disclosure includes forming a coating film partially on a base, the coating film including a calcium phosphate-based material and an antimicrobial agent.

A method of manufacturing a spinal implant according to an aspect of the present disclosure includes preparing a base and forming a coating film on the base, the coating film including a calcium phosphate-based material and an antimicrobial agent and including a first region and a sixth region having a smaller film thickness than the first region.

DESCRIPTION OF EMBODIMENTS

Embodiments according to the present disclosure will be described below with reference to the drawings.

To date, there has been no particular mention of reducing the amount of an antimicrobial metal agent included in a coating for a spinal implant to be inserted into the body. However, in a case where a coating including an antimicrobial metal agent is applied to a spinal implant to be inserted into the body, it may be preferable to reduce the amount of the antimicrobial metal agent from various points of view.

Thus, according to an aspect of the present invention, the amount of an antimicrobial metal agent can be reduced in a spinal implant coated with a coating including the antimicrobial metal agent. Specifically, details will be described below.

First Embodiment

An embodiment of the present disclosure will be described in detail below. A spinal implant according to the present embodiment is inserted between adjacent vertebrae as a replacement or a supplement of an intervertebral disk, and used to replace, correct, or restore the height of a spinal structure. Note that the spinal implant inserted between adjacent vertebrae is also referred to as, for example, an interbody spacer, block, cage, etc.

Mode of Use

Figure 1:
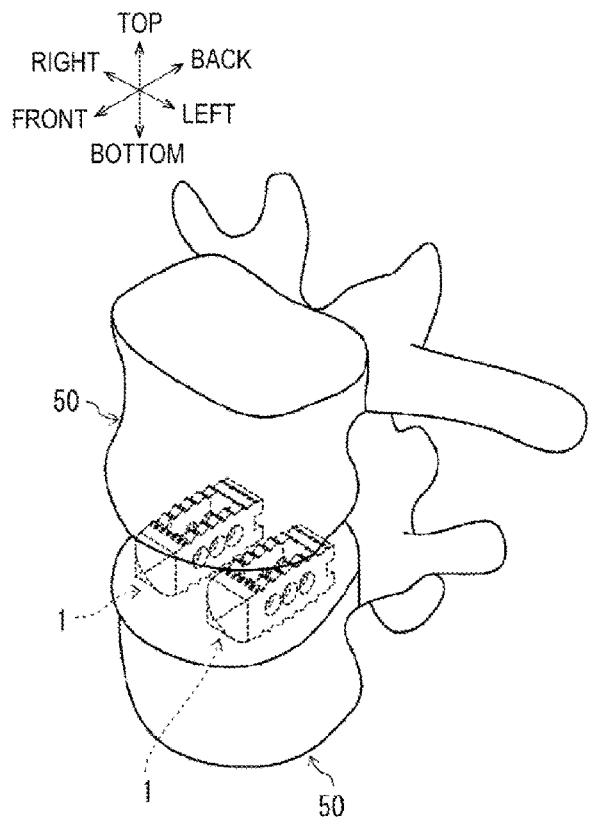
FIG. 1 is a diagram illustrating an example of a mode of use of a spinal implant according to an embodiment of the present disclosure.

First, a mode of use of a spinal implant 1 will be described with reference to FIG. 1. FIG. 1 is a diagram illustrating an example of a mode of use of the spinal implant 1. Hereinafter, for convenience of explanation, a direction indicated by an arrow denoted as "front" is referred to as a "front side" or "forward". A direction indicated by an arrow denoted as "back" is referred to as a "back side" or "rearward". A direction indicated by an arrow denoted as "top" is referred to as a "top side" or "upward". A direction indicated by an arrow denoted as "bottom" is referred to as a "bottom side" or "downward". A direction indicated by an arrow denoted as "right" is referred to as a "right side". A direction indicated by an arrow denoted as "left" is referred to as a "left side". In addition, the front side in FIG. 1 is a ventral side of a human body, and the back side in FIG. 1 is a dorsal side of the human body.

The spinal implant 1 according to the present embodiment is used in Posterior Lumbar Interbody Fusion (PLIF) or the like that is one of interbody fusion methods in surgical operations for intervertebral disk herniation or the like. In this PLIF, after a bone compressing nerves is removed to decompress the nerves, spinous processes and intervertebral joints are resected or partially resected and an intervertebral disk and cartilage endplates are removed. Then, the spinal implant 1 is inserted between adjacent vertebrae 50 so as to replace or supplement the portion where the intervertebral disk is removed.

Figure 6:
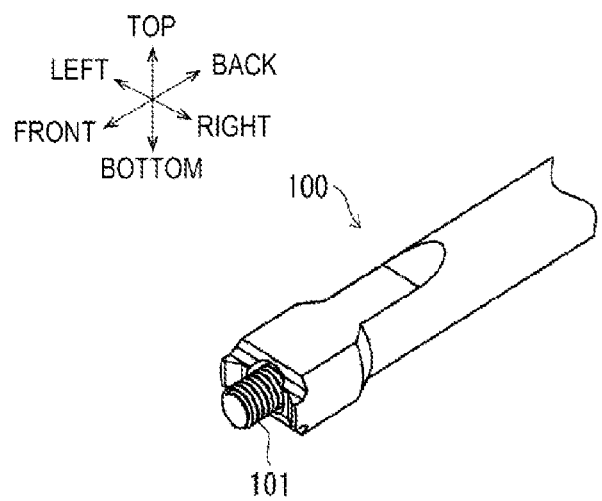
FIG. 6 is a perspective view of a holding tool for the spinal implant.

The spinal implant 1 is inserted between vertebrae from rearward, that is, from a dorsal side in a front-back direction of a human body while being held by a holding tool 100 (see FIG. 6) including a rod portion formed in a rod shape. Typically, as illustrated in FIG. 1, two spinal implants 1 are inserted between two adjacent vertebrae 50 so as to be arranged side by side in a left-right direction. Then, a metal rod (not illustrated) is attached so as to straddle the two vertebrae 50 between which the spinal implants 1 have been inserted and the metal rod is fixed to each of the two vertebrae 50, and thereby the two vertebrae 50 are fixed to each other.

The spinal implant 1 according to the present embodiment can be used, not only in PLIF, but also in other methods such as Transforaminal Lumber Interbody Fusion (TLIF), for example. In this case, the spinal implant 1 is inserted between vertebrae only on one side in a left-right direction.

Configuration of Spinal Implant 1

Figure 2:
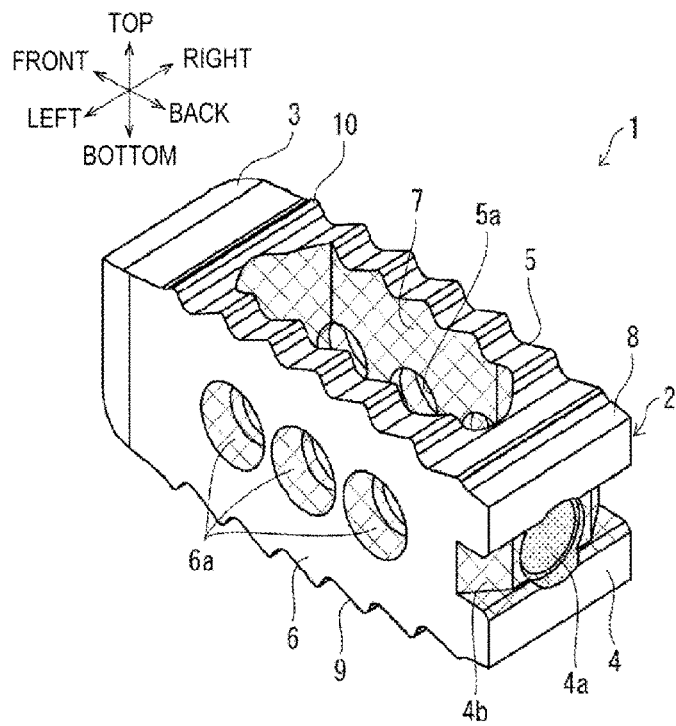
FIG. 2 is a perspective view of the spinal implant.
Figure 3:
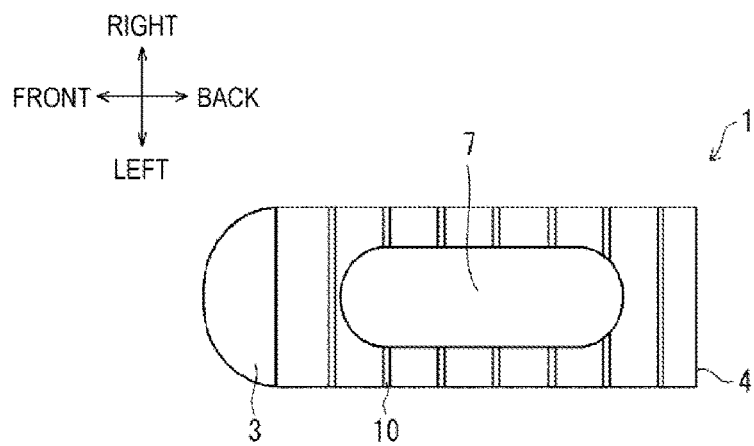
FIG. 3 is a top view of the spinal implant.
Figure 4:
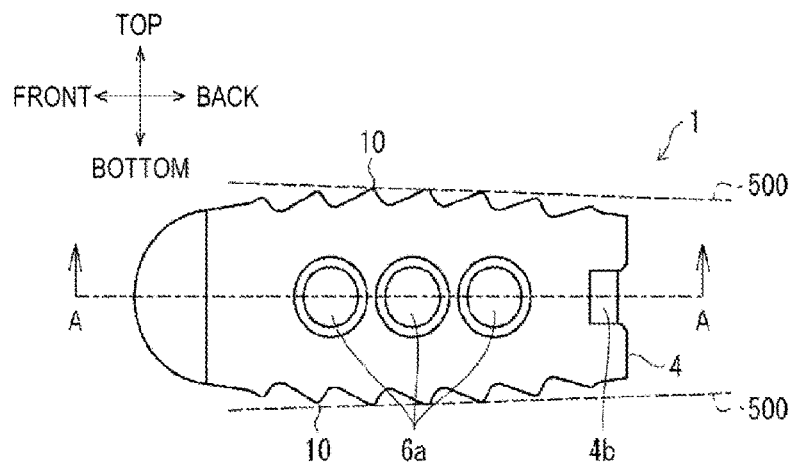
FIG. 4 is a side view of the spinal implant.
Figure 5:
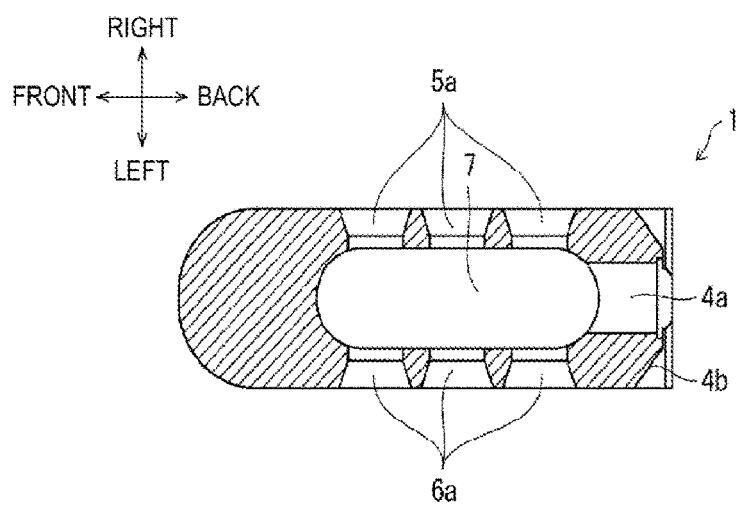
FIG. 5 is a diagram illustrating a cross-sectional plane obtained by cutting the spinal implant along a line A-A in FIG. 4.

Next, a configuration of the spinal implant 1 will be described with reference to FIGS. 2 to 5. FIGS. 2 to 5 are diagrams illustrating the configuration of the spinal implant 1, FIG. 2 is a perspective view of the spinal implant 1, FIG. 3 is a top view of the spinal implant 1, FIG. 4 is a side view of the spinal implant 1, and FIG. 5 is a diagram illustrating a cross-sectional plane obtained by cutting the spinal implant 1 along the line A-A in FIG. 4.

As illustrated in FIG. 2, the spinal implant 1 according to the present embodiment is formed by a base 2 having a substantially rectangular parallelepiped shape extending in a front-back direction, and includes a front face 3, a rear face 4, a right side face 5, a left side face 6, a top face 8, and a bottom face 9. A cavity portion 7 having an elliptical shape when viewed from the top face 8 and the bottom face 9 is provided from the top face 8 to the bottom face 9, and one or a plurality of hole portions 5a and one or a plurality of hole portions 6a are provided on the right side face 5 and the left side face 6, respectively. The shapes of the plurality of hole portions 5a and the plurality of hole portions 6a are circular shapes when viewed from the right side face 5 and the left side face 6.

Note that the shape of the spinal implant 1 is not limited to a substantially rectangular parallelepiped shape, and may be a substantially cubic shape, for example. Also, the shape of the cavity portion 7 when viewed from the top face 8 and the bottom face 9 is not limited to an elliptical shape, and may be a circular shape or a quadrangular shape, for example. In addition, the shapes of the plurality of hole portions 5a and the plurality of hole portions 6a when viewed from the right side face 5 and the left side face 6 are not limited to circular shapes, and may be quadrangular shapes, for example.

Further, the area of an opening surface (ellipse) of the cavity portion 7 is larger than the areas of opening surfaces (approximate circle) of the hole portions 5a and 6a on the side faces. The cavity portion 7 may be provided closer to the rear face 4 of the base 2. That is, the distance from the cavity portion 7 to the front face 3 may be smaller than the distance from the cavity portion 7 to the rear face 4.

Also, the hole portions 5a and 6a on the side faces may be provided closer to the rear face 4 of the base 2. That is, the distances from the hole portions 5a and 6a on the side faces to the front face 3 may be smaller than the distances from the hole portions 5a and 6a on the side faces to the rear face 4. Also, the hole portions 5a and 6a on the side faces penetrate to the cavity portion 7, and the areas of opening surfaces on a side of the right side face 5 or the left side face 6 are larger than the areas of opening surfaces on an inner surface side of the cavity portion 7. In addition, the hole portions 5a and 6a on the side faces may be tapered.

Further, a screw hole 4a (screw threads not illustrated) and a recessed portion 4b are provided on the rear face 4. The recessed portion 4b is provided so as to form a groove (notch) from the rear face 4 to the right side face 5 or the left side face 6 in the vicinity of the center of the rear face 4 in the top-bottom direction.

Here, in the present specification, for example, when the top-bottom direction of the spinal implant 1 is defined as a first direction, the cavity portion 7 can be said to be a first penetrating portion that penetrates through the base 2 in the first direction, and the spinal implant 1 can be said to include the first penetrating portion that penetrates through the base 2 in the first direction.

Also, when the left-right direction of the spinal implant 1 is defined as a second direction, the hole portions 5a and 6a that penetrate through the base 2 in the left-right direction can be said to be second penetrating portions that penetrate through the base 2 in the second direction intersecting the first direction. Then, the spinal implant 1 can be said to include the second penetrating portions that penetrate though the base 2 in the second direction intersecting the first direction.

In the present embodiment, a metal, ceramic or plastic can be used as the base 2. As examples of the metal, it is possible to use stainless steel alloys, cobalt chromium alloys, titanium, titanium alloys, and the like. As examples of titanium alloys, it is possible to use alloys added with at least one of aluminum, tin, zirconium, molybdenum, nickel, palladium, tantalum, niobium, vanadium, platinum, and the like. As examples of the ceramic, it is possible to use, for example, alumina, zirconia, an alumina-zirconia composite ceramic, and the like. As examples of the plastic, it is possible to use, for example, polyethylene, fluorine-based resin, epoxy resin, polyetheretherketone (PEEK) resin, Bakelite, and the like.

The front face 3 is formed in a wall shape that is slightly thick in the front-back direction, and a center portion thereof bulges toward a forward direction (tip) to form a convex curved surface. Further, the front face 3 has a tapered shape in which the width becomes smaller toward the tip. With such a configuration, since the front face 3 has a tapered shape, insertion of the spinal implant 1 between vertebrae can be facilitated.

The rear face 4 is formed of a flat face. As illustrated in FIG. 2, the screw hole 4a penetrating from the rear face 4 to the cavity portion 7 in the front-back direction is formed in a center portion of the rear face 4. A threaded portion 101 formed at the tip of the rod portion of the holding tool 100 for holding the spinal implant 1 is screwed into the screw hole 4a. That is, as an example, the holding tool 100 may also function as an engagement tool, and the threaded portion 101 may be configured to engage with the screw hole 4a functioning as an engagement portion.

Figure 7:
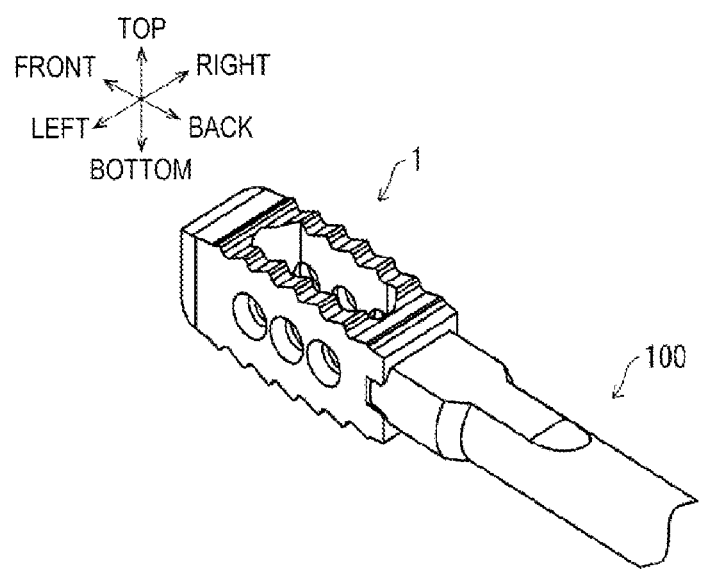
FIG. 7 is a diagram illustrating a state in which the spinal implant and the holding tool are connected.

In addition, as illustrated in FIG. 2 and the like, the recessed portion 4b is formed in the center portion of the rear face 4 in the top-bottom direction. The tip of the rod portion of the holding tool 100 comes into contact with the recessed portion 4b (see FIG. 7). Note that the screw hole 4a does not need to penetrate as long as the threaded portion 101 can be screwed. Also, the threaded portion 101 of the holding tool 100 is rotatable independently of the tip of the rod portion. By rotating only the threaded portion 101, the holding tool 100 can be attached to and detached from the spinal implant 1 while the tip of the rod portion of the holding tool 100 is left in contact with the recessed portion 4b.

Note that the spinal implant 1 is not necessarily required to be held by the holding tool 100 via the screw hole 4a. For example, the holding tool 100 may have a mechanism capable of gripping the spinal implant 1, and may hold the spinal implant 1 by gripping.

In addition, the base 2 is formed so as to become thinner from the front face 3 toward the rear face 4, in other words, such that a cross-sectional area (the area of a region surrounded by outer edges) of a plane perpendicular to the front-back direction becomes larger toward the front face 3 than toward the rear face 4. Further, the amount of change in the width of the base 2 in the left-right direction is smaller than the amount of change in the height of the base 2 in the top-bottom direction from the front face 3 toward the rear face 4. More specifically, in the present embodiment, the maximum value of the length along the left-right direction may be constant, and the maximum value of the length along the top-bottom direction may be larger in the rear face 4 than in the front face 3. The shape described above can fit into the shape of a human vertebral body.

The right side face 5 and the left side face 6 are respectively formed so as to extend in the front-back direction, and are provided so as to face each other in the left-right direction. As illustrated in FIG. 2, the hole portion 5a and 6a penetrating in the left-right direction are formed in the center portions of the right side face 5 and the left side face 6, respectively. The hole portions 5a and 6a promote blood flow near the spinal implant 1 inserted and fixed between vertebrae.

As illustrated in FIGS. 2, 3, and 5, the cavity portion 7 penetrating from the top face 8 to the bottom face 9 in the top-bottom direction is formed in the spinal implant 1. The cavity portion 7 is filled with a bone forming material.

As illustrated in FIGS. 2 to 4, a plurality of protruding tooth portions 10 are formed on the top face 8. The protruding tooth portions 10 protrude upward from the top face 8 and extend in the left-right direction within the surface of the top face 8. Similarly, a plurality of protruding tooth portions 10 are formed on the bottom face 9. The protruding tooth portions 10 protrude downward from the bottom face 9 and extend in the left-right direction within the surface of the bottom face 9. That is, the pluralities of protruding tooth portions 10 are provided as tooth portions respectively protruding from the faces 8 and 9.

In this case, as described above, "the base 2 is formed so as to become thinner from the front face 3 toward the rear face 4" means that the height of vertex of the protruding tooth portions 10 along the top-bottom direction becomes smaller toward the rear.

In addition, the plurality of protruding tooth portions 10 disposed on the top face 8 and the plurality of protruding tooth portions 10 disposed on the bottom face 9 may be respectively located at positions corresponding to each other in the top-bottom direction. That is, one protruding tooth portion 10 disposed on the bottom face 9 may be located under one protruding tooth portion 10 disposed on the top face 8.

The protruding tooth portion 10 is formed such that an inclination (slope) in a forward direction is gentler (smaller) than an inclination (slope) in a rearward direction. When the top face 8 and the bottom face 9 of the spinal implant 1 are in contact with the vertebrae 50, the movement of the spinal implant 1 in the forward direction is facilitated and the movement in the rearward direction is complicated.

By providing the protruding tooth portions 10 in this manner, a positional shift of the spinal implant 1 can be prevented, and backout (to be described later) can also be prevented.

In addition, the height of the front face 3 in the top-bottom direction is smaller than the height of a portion of the protruding tooth portions 10 in the top-bottom direction, and the rear face 4 is present inside extension lines of imaginary lines connecting the vertices of the protruding tooth portions 10.

The imaginary lines connecting the vertices of the plurality of protruding tooth portions 10 may be curved lines. In a case where the imaginary lines connecting the vertices of the plurality of protruding tooth portions 10 are curved lines, the vertices of the curved lines (imaginary curves) may be located on a side of the front face 3. That is, the distance between the vertices of the imaginary curves and the front face 3 may be smaller than the distance between the vertices of the imaginary curves and the rear face 4.

In the spinal implant 1 according to the present embodiment, a coating film including a calcium phosphate-based material and an antimicrobial agent is not disposed on the entirety of the spinal implant 1, but the spinal implant 1 includes a first region on which the coating film is disposed and a second region exposed from the coating film.

The first region on which the coating film including the calcium phosphate-based material and the antimicrobial agent is disposed and the second region exposed from the coating film can be distinguished from each other by an elemental analysis of the surface of each region. The elemental analysis method can be implemented, for example, by mapping surface elements using an energy dispersive X-ray (EDX) analyzer that is an auxiliary device of a general scanning electron microscope (SEM). Alternatively, surface analysis methods such as X-ray photoelectron spectroscopy, Auger electron spectroscopy, and secondary ion mass spectrometry may be used. Still alternatively, a sample obtained by mechanically scraping off the surface of each region may be chemically analyzed to detect elements. From the surface of the first region, phosphorus, calcium, antimicrobial components, and the like are detected. From the surface of the second region, elements constituting the base member are detected, but phosphorus, calcium, antimicrobial components, and the like are not detected, or are at a noise level or lower.

For example, among the surfaces of the spinal implant 1, the coating film is not disposed in a region of the screw hole 4a (the second region), and the coating film is disposed only in a region other than the screw hole 4a (the first region). In this case, in the region of the screw hole 4a, a base surface of the spinal implant 1 is directly exposed. The second region may include the entirety of the screw hole 4a, or may include a part of the screw hole 4a. Also, the second region is not limited to the screw hole 4a, and may be other portions of the spinal implant 1. Note that the portion of the base surface exposed from the coating film (the second region) only needs to be exposed from the coating film, and may have a film or a layer different from the coating film formed thereon.

Accordingly, this allows the spinal implant 1 to get the benefit of having the coating film, while reducing the likelihood of the coating film being peeled off and brought into the body.

As for the coating film of the spinal implant 1, the film thickness in the boundary portion between the top face 8 and the right side face 5 or the left side face 6, or the boundary portion between the bottom face 9 and the right side face 5 or the left side face 6 may be thicker than the film thickness in other regions. That is, the coating film can be formed to be thicker in corner portions of the base.

Also, for the coating film of the cavity portion 7 of the spinal implant 1, the film thickness at the edge of the opening of the cavity portion 7 may be thicker than the film thickness at the inner surface of the cavity portion 7. In addition, the coating film may be formed such that the film thickness becomes thinner from the opening toward the inner side of the cavity portion 7.

Preparation of Base

Next, a method of manufacturing the spinal implant 1 will be described. First, the base 2 is prepared to manufacture the spinal implant 1. The base 2 can be formed, for example, by cutting a mass such as a round bar out of a metal material through a machining process. By performing the machining process, the base including constituent elements such as the front face 3, the rear face 4, the top face 8, the bottom face 9, the right side face 5, the left side face 6, the cavity portion 7, and the hole portions 5a and 6a can be prepared. That is, the base constituting the spinal implant 1 is provided with the cavity portion 7 penetrating in the top-bottom direction, the hole portions 5a and 6a on the right and left side faces, and the screw hole 4a on the rear face (a step of forming an engagement portion and a step of forming holes). Note that the base 2 may be formed by machining a ceramic or a resin mass, or may be formed by a method different from machining.

Coating Method

Next, a coating method for the spinal implant 1 will be described. In the spinal implant 1 according to the present embodiment, the coating film is formed by the thermal spraying of a material including a calcium phosphate-based material and an antimicrobial agent onto the base. The antimicrobial agent is silver for example, and the silver concentration in the thermal spray coating film is from 0.05 wt % to 3.00 wt %, for example. As the calcium phosphate-based material, one type or two types or more of mixtures selected from the group consisting of hydroxyapatite, α-tertiary calcium phosphate, β-tertiary calcium phosphate, quaternary calcium phosphate can be used.

Examples of the thermal spraying method for forming a thermal spray coating film including a calcium phosphate-based material include a flame spraying method, a high-speed flame spraying method, a plasma spraying method, and a cold spraying method. For example, in the flame spraying method, a thermal spraying material is brought into a molten or nearly molten state by using a gas flame of oxygen and a combustible gas as a heat source, and sprayed onto the surface of a base material to form a coating film. In an ordinary flame spraying method, the spray temperature is about 2700° C., and the spraying speed is Mach 0.6. As thermal spraying conditions, for example, thermal spraying powder can be introduced into a gas flame torch of 50 psi oxygen gas and 43 psi acetylene gas using 100 psi dry air, and the thermal spraying can be performed at a spraying distance of 60 to 100 mm.

The thickness of a thermal spray coating film is from 5 to 100 µm, and preferably from 20 to 40 µm. This is because when the thickness is 5 µm or more, an entire spray area can be covered, and when the thickness is 100 µm or less, the adhesion strength of the coating film is not decreased due to residual stress at the time of spraying.

In the present embodiment, the thermal spray coating film of the calcium phosphate-based material including the antimicrobial material is formed such that powder of the coating film material in a molten (or a semi-molten) state is sprayed onto the base material (the base), and cooled, solidified, and accumulated thereon. Therefore, the thermal spray coating film may be referred to as a sprayed layer or a coating layer.

The thermal spray coating film formed may be subjected to heat treatment. This is because the crystallinity of the calcium phosphate-based material can be increased and the stability of the coating film can be improved. Heat treatment is performed for 0.5 to 7 hours under a reduced pressure of $10^{-2}$ Pa or less, and within a temperature range of from 400 to 1000° C. A temperature range of from 550 to 850° C., and a time period of from 1 to 5 hours are preferable.

After the heat treatment, the thermal spray coating film may be subjected to a hydration treatment. By performing the hydration treatment, oxyapatite is transformed into hydroxyapatite, and silver ion elution can be stabilized. The hydration treatment is a step of adding water molecules to a substance, and can be performed, for example, by immersing the substance in water at 60 to 100° C. for 10 to 60 minutes.

The silver concentration in the thermal spray coating film can be adjusted by changing the amount of the silver material mixed with the calcium phosphate-based material that is the thermal spraying material. The silver concentration in the thermal spray coating film is from 0.05 wt % to 3.00 wt %, preferably from 0.05 wt % to 2.50 wt %, more preferably from 0.05 wt % to 1.00 wt %, and still more preferably from 0.1 wt % to 1.00 wt %. This is because the antimicrobial effect is sufficient when the concentration is 0.05% or more by weight. In addition, when the concentration is 3.00% or less by weight, the impact on living tissue can be reduced.

A coating step for the spinal implant 1 is as follows. A coating film including a calcium phosphate-based material and an antimicrobial agent is partially formed on the base (step of forming the coating film). Note that a region where the coating film including the calcium phosphate-based material and the antimicrobial agent is partially formed on the base is the first region, and a region of the base where the coating film is not formed is the second region. In the step of forming the coating film, the coating film is formed in a state in which a screw for the step of forming the coating film is inserted in the screw hole 4a, and then the screw is removed. Accordingly, the coating film can be formed except for at the screw hole 4a. When the second region is disposed throughout the screw hole 4a, the screw hole 4a is completely filled with the screw for the step of forming the coating film. The screw for the step of forming the coating film is disposed so as to penetrate through the screw hole 4a, for example. In a case where roughening is performed, the roughening may be performed before forming the coating film (a roughening step).

The method of forming the coating film is not limited to thermal spraying methods such as a flame spraying method, a high-speed flame spraying method, and a plasma spraying method. Physical vapor deposition methods such as a sputtering method, an ion plating method, an ion beam deposition method, and an ion mixing method, or wet coating methods such as a sol-gel method may be selected.

The coating film may be disposed directly on the base 2 by any of the methods described above, or may be disposed via an intermediate layer as described below. That is, a film may be formed as an intermediate layer on a base surface by methods such as coating, plating, thermal spraying, and vapor deposition, and then the above-described coating film of a calcium phosphate-based material may be further formed on the intermediate layer. As a method of forming an intermediate layer, an additive manufacturing method may be used.

The intermediate layer may be a metal, a polymer or a ceramic. For example, after an intermediate layer of a titanium metal is formed on a desired surface of a base made of a PEEK resin, the coating film including a calcium phosphate-based material and an antimicrobial agent may be formed on the surface of the intermediate layer.

Method of Insertion Between Vertebrae

Next, a procedure for inserting the spinal implant 1 according to the present embodiment between vertebrae will be described.

First, before inserting the spinal implant 1 between vertebrae, an operator sets the spinal implant 1 to the holding tool 100 for holding the spinal implant 1. Specifically, while the rod portion of the holding tool 100 is inserted in the recessed portion 4b of the spinal implant 1, the threaded portion of the holding tool 100 is screwed into the screw hole 4a of the spinal implant 1. Thereby, the spinal implant 1 is positioned with respect to the holding tool 100 and the spinal implant 1 is held. Note that the cavity portion 7 of the spinal implant 1 is filled with a bone forming material.

Next, the operator inserts the spinal implant 1 between the vertebrae. Specifically, the operator inserts the front face 3 side of the spinal implant 1 between the vertebrae from which a bone compressing nerves, an intervertebral disk, and the like have been removed, from the dorsal side of the human body. Then, after the spinal implant 1 is placed on one of a right or left side (for example, the right side) between the adjacent vertebrae 50, the holding tool 100 is detached from the spinal implant 1, so that the spinal implant 1 is installed on the right side between the vertebrae. In a case where the installation position of the spinal implant 1 is shallower than the position expected before the operation, the installation position is adjusted by driving in the spinal implant 1 with a driving tool (impactor). In a similar way, the operator installs the spinal implant 1 on a left side portion between the adjacent vertebrae.

Then, the operator attaches a metal rod (not illustrated) so as to straddle the adjacent vertebrae and fix the rod to each of the vertebrae 50. Accordingly, the adjacent vertebrae 50 can be fixed to each other. After the operation, the bone forming material filled in the cavity portion 7 is fused to the upper and the lower vertebrae 50, and the adjacent vertebrae 50 are rigidly fixed.

Generally, in an early stage of fixation of a spinal cage between vertebrae, or in a state in which a bone forming material filled in a cavity portion has not been sufficiently fused to the vertebrae, a problem of backout may occur. The term backout refers to shifting and displacement of the spinal implant 1 installed at a predetermined position between the vertebrae toward the dorsal side (rearward) of a patient.

In the spinal implant 1 according to the present embodiment, the inclination of the protruding tooth portions 10 provided on the top face 8 and the bottom face 9 is steeper at the rear side than at the front side. This makes it difficult for the spinal implant 1 to move rearward, and can prevent backout of the spinal implant 1.

Roughening

A part of the surface of the spinal implant 1 may be roughened so as to provide a rough surface portion. For example, the top face 8 and the bottom face 9 of the spinal implant 1 may be roughened. The roughening can be performed by, for example, using at least one of thermal spraying or blasting. As a thermal spraying material, materials that have been exemplified as a material of the base 2 can be used. The blasting includes sandblasting and the like. It is also possible to perform roughening by forming a porous structure or the like on the surfaces of the spinal implant 1 using a 3D printer or the like. By roughening the top face 8 and the bottom face 9, the roughened portions are brought into contact with a spine, and thus the fixation performance between the spinal implant 1 and the spine can be increased.

In a case where a rough surface is formed, the roughening may be performed before forming the coating film. Thereafter, the coating film may be formed on the rough surface formed.

Rough surfaces may be formed by roughening each surface of the base. Specifically, the top face 8 and the bottom face 9 can be roughened from the first direction to form rough surfaces, and the right side face 5 and the left side face 6 can be roughened from the second direction to form rough surfaces. Then, the front face 3 can be roughened from a third direction (front-back direction) intersecting the first direction and the second direction to form a rough surface.

Note that, depending on the shape of the front face 3, a rough surface having a sufficient roughness may also be formed on the front face 3 by the roughening performed on the top face 8, the bottom face 9, the right side face 5, and the left side face 6. In that case, the roughening of the front face 3 may be omitted.

Also, rough surfaces may be formed on the respective inner surfaces of the cavity portion 7 and the hole portions 5a and 6a.

Note that, depending on the shape of the cavity portion 7 and the hole portions 5a and 6a, and depending on the direction of thermal spraying or sand blasting, the coating film including the first region and the second region may be formed by simultaneously performing thermal spraying or the like on outer surfaces of the coating film (the top face 8, the bottom face 9, the right side face 5, and the left side face 6) and thermal spraying on the inner surfaces of the cavity portion 7 and the hole portions 5a and 6a.

Variation

In the present embodiment, the spinal implant 1 is held by the holding tool 100 by screwing together the holding tool 100 and the spinal implant 1, but the holding of the spinal implant 1 by the holding tool 100 is not limited to screwing.

For example, a locking mechanism including a recessed portion or a protruding portion may be provided in the base 2 of the spinal implant 1, and a part of the holding tool 100 may be fitted to the locking mechanism and locked to hold the spinal implant 1. Specifically, for example, it may be possible to employ a mechanism in which the base is provided with a hole whose diameter is larger in an inner portion than in an opening portion, a tip of the holding tool is provided with a variable outer diameter mechanism, and the tip of the holding tool is inserted into the hole with the outer diameter of the tip contracted and then locked by expanding the outer diameter of the tip inside the hole. That is, the holding tool 100 may also function as an engagement tool, and the hole (engagement portion) engaging with the holding tool may include a locking mechanism for locking the holding tool 100 and the base 2. Note that the spinal implant may be locked and held by a holding tool that clamps a part of the base.

In the present embodiment, the second region exposed from the coating film has been described as a region of the screw hole 4a. Here, the entirety of the region of the screw hole 4a along the depth direction may be included in the second region; however, only a part of the region may be included in the second region. However, a side of the region from which the holding tool 100 is inserted is preferably included in the second region. The second region is not limited to the region of the screw hole 4a, but may include a region of the locking mechanism or the engagement portion described above. Also, the second region is not limited to these regions, and may include a region that comes into contact with a part of the holding tool 100 or a region that slides with a part of the holding tool 100 when the spinal implant 1 is held by the holding tool 100. Regions other than the regions described above are preferably included in the first region in which the coating film is disposed, but the second region exposed from the coating film may be provided in regions other than the regions described above.

In the present embodiment, as a spinal implant according to the present disclosure, the spinal implant 1 inserted between adjacent vertebrae has been described. However, a spinal implant according to the present disclosure is not limited to the spinal implant 1 described above. For example, a spinal rod (a rod for fixing a spine in a constant shape), a spinal screw (a screw to be screwed into a vertebra to fix the spinal rod to the spine), and the like for fixing the spinal implant 1 inserted between vertebrae are included in the spinal implant according to the present disclosure. In this case, the second region exposed from the coating film is preferably set in a region where members (for example, the spinal rod and the spinal screw) come into contact with each other or slide against each other.

Second Embodiment

Another embodiment of the present disclosure will be described below. Note that, for convenience of description, a member having the same function as that of a member described in the embodiments described above is denoted by the same reference sign, and description thereof will not be repeated. That is, configurations not mentioned in the present embodiment are equivalent to the configurations in the first embodiment described above.
Configuration of Spinal Implant 1

In the spinal implant 1 according to the present embodiment, the coating film including a calcium phosphate-based material and an antimicrobial agent is not disposed on the entirety of the spinal implant 1, and the spinal implant 1 may include the first region in which the coating film is disposed and a sixth region in which the film thickness of the coating film is smaller than the film thickness in the first region.

In the present embodiment, for example, the front face 3, a part of the rear face 4 (the portion excluding the screw hole 4a and the recessed portion 4b), the top face 5, the bottom face 9, the right side face 5, and the left side face 6 of the spinal implant 1 are included in the first region in which the coating film is disposed. On the other hand, the inner surfaces of the hole portions 5a and 6a, the inner surface of the cavity portion 7, and the recessed portion 4b are included in the sixth region in which the coating film having a film thickness smaller than the film thickness in the first region is disposed.

In this way, the first region may include the outer peripheral surfaces of the base 2, and the sixth region may include the inner surface of the cavity portion 7 and the inner surfaces of the hole portions 5a and 6a. Accordingly, the spinal implant 1 can reduce the total amount of the coating film as compared with a case where the entirety of the spinal implant 1 is coated with the coating film, while enjoying the benefit having the coating film.

In addition, since the coating film includes the sixth region having a film thickness smaller than the film thickness in the first region, the coating film in the sixth region can be easily formed as compared to the coating film in the first region, and thus the manufacturing efficiency of the spinal implant 1 can be improved.

The spinal implant 1 further includes a third region in which the film thickness of the coating film is smaller than the film thickness in the sixth region, or which is not coated with the coating film (exposed from the coating film). Note that the third region corresponds to the second region in the first embodiment described above. In the present embodiment, the screw hole 4a is the third region in which the coating film is not disposed. In this case, in the region of the screw hole 4a, a base surface of the spinal implant 1 is directly exposed. The third region may include the entirety of the screw hole 4a, or may include a part of the screw hole 4a. Also, the third region is not limited to the screw hole 4a, and may include other portions of the spinal implant 1. Note that the portion of the base surface exposed from the coating film (the third region) only needs to be exposed from the coating film, and may have a film or a layer different from the coating film formed thereon.
Coating Method A coating step for the spinal implant 1 is as follows. The coating film is formed so as to have different film thicknesses (a step of forming the coating film). Accordingly, as for the coating film, the first region and the sixth region having different film thicknesses can be formed. The coating film can be formed by applying a thermal spray coating film on each surface of the base 2. In a case where the coating film is formed by thermal spraying, the film thickness of the coating film on the base 2 can be changed by adjusting thermal spraying conditions such as spraying time, spraying direction, composition of the thermal spraying material, and spraying temperature. For example, an increase in the film thickness of the coating film of the base 2 can be achieved by lengthening the spraying time, and a decrease in the film thickness of the coating film of the base 2 can be achieved by shortening the spraying time.

Specifically, the top face 8 and the bottom face 9 can be thermal-sprayed from the first direction to form the coating film, and the right side face 5 and the left side face 6 can be thermal-sprayed from the second direction to form the coating film. Then, the front face 3 can be thermal-sprayed from the third direction (front-back direction) intersecting the first direction and the second direction to form the coating film. In this manner, the first region of the coating film can be formed on each surface of the base 2.

Note that, depending on the shape of the front face 3, a coating film having a sufficient film thickness may also be formed on the front face 3 by the thermal spraying performed on the top face 8, the bottom face 9, the right side face 5, and the left side face 6. In that case, the thermal spraying on the front face 3 may be omitted.

Also, the coating film is formed on the respective inner surfaces of the cavity portion 7 and the hole portions 5a and 6a. In the thermal spraying on the cavity portion 7 and the hole portions 5a and 6a, the coating film of the sixth region having a film thickness smaller than the film thickness of the first region can be formed by shortening the irradiation time as compared with the case of forming the first region of the coating film. Alternatively, the sixth region of the coating film may be formed, for example, by reducing the amount of spraying material as compared with the case of forming the first region.

Note that, depending on the shape of the cavity portion 7 and the hole portions 5a and 6a, and depending on the direction of thermal spraying, the coating film including the first region and the sixth region may be formed by simultaneously performing the thermal spraying on outer surfaces of the coating film (the top face 8, the bottom face 9, the right side face 5, and the left side face 6) and the thermal spraying on the inner surfaces of the cavity portion 7 and the hole portions 5a and 6a. That is, the film thickness of the first region and the film thickness of the sixth region can be formed by performing the thermal spraying on the base 2 in consideration of the shape of the base 2 and the expected distribution amount of the thermal spraying material.

The coating film is also formed on the inner surface of the recessed portion 4b of the rear face 4. In the thermal spraying on the recessed portion 4b, the coating film of the third region having a film thickness smaller than the film thickness of the sixth region can be formed by shortening the irradiation time as compared with the case of forming the second region of the coating film. Alternatively, the third region of the coating film may be formed, for example, by reducing the amount of spraying material as compared with the case of forming the sixth region. Note that, depending on thermal spraying conditions, the third region of the coating film may be formed simultaneously with the first region and the sixth region. Also, the rear face 4 excluding the recessed portion 4b may be included in the first region or the sixth region of the coating film.

Note that, in the step of forming the coating film, the coating film is formed in a state in which a screw for the step of forming the coating film is inserted in the screw hole 4a, and then the screw is removed. Accordingly, the coating film can be formed except for at the screw hole 4a. When the sixth region is disposed throughout the screw hole 4a, the screw hole 4a is completely filled with the screw for the step of forming the coating film. The screw for the step of forming the coating film is disposed so as to penetrate through the screw hole 4a, for example. This may form the third region of the coating film. In a case where roughening is performed, the roughening may be performed before forming the coating film (a roughening step).

Roughening

Rough surfaces may be formed by roughening each surface of the base. Specifically, the top face 8 and the bottom face 9 can be roughened from the first direction to form rough surfaces, and the right side face 5 and the left side face 6 can be roughened from the second direction to form rough surfaces. Then, the front face 3 can be roughened from a third direction (front-back direction) intersecting the first direction and the second direction to form a rough surface. In this manner, a fourth region that is a rough surface can be formed on each of the faces of the base 2.

Note that, depending on the shape of the front face 3, a rough surface having a sufficient roughness may also be formed on the front face 3 by the roughening performed on the top face 8, the bottom face 9, the right side face 5, and the left side face 6. In that case, the roughening of the front face 3 may be omitted.

Also, a rough surface is formed on the respective inner surfaces of the cavity portion 7 and the hole portions 5a and 6a. In the roughening of the cavity portion 7 and the hole portions 5a and 6a, a fifth region that is a rough surface having a roughness smaller than the roughness of the fourth region can be formed by shortening the roughening time as compared with the case of forming the fourth region that is a rough surface. Alternatively, the fifth region that is a rough surface may be formed, for example, by reducing the amount of spraying material or the amount of a sandblast material as compared with the case of forming the fourth region.

Note that, depending on the shape of the cavity portion 7 and the hole portions 5a and 6a, and depending on the direction of thermal spraying or sand blasting, the coating film including the first region and the sixth region may be formed by simultaneously performing the thermal spraying or the like on outer surfaces of the coating film (the top face 8, the bottom face 9, the right side face 5, and the left side face 6) and the thermal spraying on the inner surfaces of the cavity portion 7 and the hole portions 5a and 6a.

Note that, since the first region described above corresponds to the front face 3, the rear face 4, the top face 8, the bottom face 9, the right side face 5, and the left side face 6 of the spinal implant 1, the first region may overlap with the fourth region. Also, since the sixth region corresponds to the inner surface of the cavity portion 7 and the inner surfaces of the hole portions 5a and 6a, the sixth region may overlap with the fifth region.

Variation

In the present embodiment, the third region exposed from the coating film has been described as a region of the screw hole 4a. Here, the entirety of a region along the depth direction of the screw hole 4a may be included in the third region, but only a part of the region may be included in the third region. However, a side of the region from which the holding tool 100 is inserted is preferably included in the third region. The third region is not limited to the region of the screw hole 4a, but may include a region of the locking mechanism or the engagement portion described above. Also, the third region is not limited to these regions, and may include a region that comes into contact with a part of the holding tool 100 or a region that slides with a part of the holding tool 100 when the spinal implant 1 is held by the holding tool 100. Regions other than the regions described above are preferably included in the first region or the sixth region in which the coating film is disposed, but the third region exposed from the coating film may be provided in regions other than the regions described above.

In addition, in the present embodiment, the inner surfaces of the hole portions 5a and 6a, the inner surface of the cavity portion 7, and the recessed portion 4b are included in the sixth region, but the recessed portion 4b may be included in the first region. Also, except for the screw hole 4a, surfaces that do not face the outside may be included in the sixth region.

In the present embodiment, as a spinal implant according to the present disclosure, the spinal implant 1 inserted between adjacent vertebrae has been described. However, a spinal implant according to the present disclosure is not limited to the spinal implant 1 described above. For example, a spinal rod (a rod for fixing a spine in a constant shape), a spinal screw (a screw to be screwed into a vertebra to fix the spinal rod to the spine), and the like for fixing the spinal implant 1 inserted between vertebrae are included in the spinal implant according to the present disclosure. In this case, the third region exposed from the coating film is preferably configured to include regions where members (for example, the spinal rod and the spinal screw) come into contact with each other or slide against each other.

The present disclosure is not limited to the embodiments described above, and various modifications can be made within the scope indicated by the claims, and an embodiment obtained by appropriately combining technical means disclosed in different embodiments is also included in a technical scope of the present disclosure. Further, new technical features can be formed by combining the technical means respectively disclosed in the embodiments.

CONCLUSION

A spinal implant according to an aspect of the present disclosure includes a base and a coating film disposed on the base and including a calcium phosphate-based material and an antimicrobial agent, in which a surface of the base includes a first region and a second region, the first region being disposed with the coating film, and the second region being exposed from the coating film.

The calcium phosphate-based material in the coating film has an effect of improving bone conduction and bone fixation properties. The antimicrobial agent in the coating film has an effect of reducing adhesion and growth of bacteria.

According to the configuration described above, since the spinal implant can be inserted into the body at the time of a surgery operation or the like by being held by the second region of the base exposed from the coating film, the coating film is less likely to be peeled off from a held portion at the time of inserting the spinal implant and removing the holding tool. Thus, it is possible to reduce the likelihood of the coating film being peeled off and taken into the body, as compared with a case where the entire surfaces of the base are coated.

The spinal implant according to an aspect of the present disclosure may further include an engagement portion disposed in the second region and configured to engage with an engagement tool.

According to the configuration described above, since the engagement portion configured to engage with the engagement tool is provided in the second region, it is possible to prevent the coating film from being peeled off at the time of engagement.

In the spinal implant according to an aspect of the present disclosure, the engagement portion may include a locking mechanism including a recessed portion or a protruding portion configured to lock the engagement tool and the base.

According to the configuration described above, it is possible to lock the engagement tool and the base by the locking mechanism including the recessed portion or the protruding portion without using an adhesive agent, a magnetic force, or the like.

In the spinal implant according to an aspect of the present disclosure, the engagement portion may include a screw hole. "the second region may include" as in claim 4.

According to the configuration described above, it is possible to easily attach the spinal implant to a holding tool and easily detach the spinal implant by using the screw hole.

In the spinal implant according to an aspect of the present disclosure, the base may include a rough surface portion obtained by roughening, and the coating film may cover at least a part of the rough surface portion.

According to the configuration described above, it is possible to improve the fixation performance between the spinal implant and a spine by bringing the rough surface portion into contact with the spine.

In the spinal implant according to an aspect of the present disclosure, the coating film is preferably disposed directly on the base.

According to the configuration described above, the configuration of the spinal implant is simplified, and thus the manufacturing cost can be suppressed.

A method of manufacturing a spinal implant according to an aspect of the present disclosure includes forming a coating film partially on a base, the coating film including a calcium phosphate-based material and an antimicrobial agent.

The method of manufacturing a spinal implant according to an aspect of the present disclosure may further include forming an engagement portion configured to engage with an engagement tool in the base before forming the coating film, and, in the forming of the coating film, the coating film may be formed except for at the engagement portion.

The method of manufacturing a spinal implant according to an aspect of the present disclosure may further include forming a screw hole in the base before forming the coating film, and, in the forming of the coating film, the coating film may be formed on the base except for at the screw hole.

The method of manufacturing a spinal implant according to an aspect of the present disclosure may further include forming a rough surface portion on at least a part of a surface of the base before forming the coating film, and, in the forming of the coating film, the coating film may be formed so as to cover at least a part of the rough surface portion.

In the method of manufacturing a spinal implant according to an aspect of the present disclosure, in the forming of the rough surface, the rough surface may be formed by at least one of thermal spraying and blasting.

A spinal implant according to an aspect of the present disclosure includes a base and a coating film disposed on the base and including a calcium phosphate-based material and an antimicrobial agent, in which the coating film includes a first region and a sixth region having a smaller film thickness than the first region.

The calcium phosphate-based material in the coating film has an effect of improving bone conduction and bone fixation properties. Also, the antimicrobial agent in the coating film has an effect of reducing adhesion and growth of bacteria. However, since the cost of an antimicrobial metal agent is also high, the amount thereof is preferably as small as possible. Then, according to the configuration described above, since the film thickness of a region of the coating film is made thinner than that of other regions, the total amount of the antimicrobial metal agent can be reduced as compared with a case where the film thickness is not made thinner. This makes it possible to reduce the cost, for example.

A spinal implant according to an aspect of the present disclosure may further include a first penetrating portion penetrating through the base in a first direction.

According to the configuration described above, the first penetrating portion can be filled with a bone forming material, and thus the connection between the spinal implant and vertebrae can be facilitated.

In the spinal implant according to an aspect of the present disclosure, the first region may be located on an outer peripheral surface of the base, and the sixth region may be located on an inner surface of the first penetrating portion.

According to the configuration described above, the film thickness of the coating film on the inner surface of the first penetrating portion is smaller than the film thickness of the coating film on the outer peripheral surface, and thus the total amount of silver included in an antimicrobial agent can be reduced while the antimicrobial effect can be maintained in regions that are likely to directly contact vertebrae.

In the spinal implant according to an aspect of the present disclosure, the coating film may include a third region having a smaller film thickness than the sixth region, and the first region and the third region may be located on an outer peripheral surface of the base.

In the configuration described above, when the third region is a holding portion for holding the spinal implant, peeling off of the coating film associated with the holding of the spinal implant can be suppressed. Thus, according to the configuration described above, it is possible to prevent the coating film from being peeled off and taken into the body in association with the holding of the spinal implant.

In the spinal implant according to an aspect of the present disclosure, a surface of the base may include a fourth region and a fifth region having a smaller surface roughness than the fourth region.

According to the configuration described above, it is possible to reduce the surface roughness of a predetermined region of the base, as necessary.

In the spinal implant according to an aspect of the present disclosure, the first region may overlap with the fourth region.

According to the configuration described above, a region belonging to both of the first region and the fourth region can be provided.

In the spinal implant according to an aspect of the present disclosure, the sixth region may overlap with the fifth region.

According to the configuration described above, a region belonging to both of the sixth region and the fifth region can be provided.

The spinal implant according to an aspect of the present disclosure may further include a second penetrating portion that penetrates through the base in a second direction that is a direction intersecting the first direction.

According to the configuration described above, blood flow can be promoted via the second penetrating portion.

In the spinal implant according to an aspect of the present disclosure, the second penetrating portion may include a plurality of through holes disposed separately from each other.

According to the configuration described above, blood flow can be promoted via the plurality of through holes.

In the spinal implant according to an aspect of the present disclosure, the sixth region may be located on an inner surface of the second penetrating portion.

According to the configuration described above, it is possible to reduce the film thickness of the coating film on the inner surface of the second penetrating portion that is less likely to directly contact vertebrae.

A method of manufacturing a spinal implant according to an aspect of the present disclosure includes preparing a base and forming a coating film on the base, the coating film including a calcium phosphate-based material and an antimicrobial agent and including a first region and a sixth region having a smaller film thickness than the first region.

In the method of manufacturing a spinal implant according to an aspect of the present disclosure, in the forming of the coating film, the coating film further including a third region having a smaller film thickness than the sixth region may be formed.

The method of manufacturing a spinal implant according to an aspect of the present disclosure may include forming a rough surface on at least a part of the surface of the base before forming the coating film.

In the method of manufacturing a spinal implant according to an aspect of the present disclosure, in the forming of the coating film, the coating film may be formed to cover at least a part of the rough surface.

In a method of manufacturing a spinal implant according to an aspect of the present disclosure, the rough surface may be formed by at least one of thermal spraying and blasting at the step of forming the rough surface.

REFERENCE SIGNS LIST

1 Spinal implant
2 Base
3 Front face
4 Rear face
4a Screw hole (engagement portion, locking mechanism)
4b Recessed portion
5 Right side face
5a Hole portion
6 Left side face
6a Hole portion
7 Cavity portion
8 Top face
9 Bottom face
10 Protruding tooth portion
100 Holding tool (engagement tool)
101 Threaded portion

The invention claimed is:

1. A spinal implant comprising:
a base made of metal material and including a top face, a bottom face, and a side face; and
a coating film disposed on the base, the coating film comprising a calcium phosphate-based material and an antimicrobial agent, wherein
a surface of the base comprises a first region and a second region, the first region being disposed with the coating film, and the second region being disposed with no coating film,
part of the first region is located in the side face,
the first region further comprises a first location having a smaller coating film thickness than a second location of the first region, and
the first location is at least one of
(a) an inner surface of a first penetrating portion penetrating through the base in a first direction,
(b) an inner surface of a second penetrating portion penetrating through the base in a second direction that intersects the first direction, or
(c) a recessed portion provided on a rear face of the base.

2. The spinal implant according to claim 1, further comprising:
an engagement portion disposed in the second region, the engagement portion configured to engage with an engagement tool.

3. The spinal implant according to claim 2, wherein the engagement portion comprises a locking mechanism; and the locking mechanism comprises a recessed portion or a protruding portion configured to lock the engagement tool and the base.

4. The spinal implant according to claim 3, wherein
the locking mechanism comprises a hole portion in the second region and a tip portion,
a diameter of an inner portion of the hole portion is larger than a diameter at an opening portion of the hole portion, and
the tip portion is disposed in the engagement tool, is configured to be inserted into the hole portion, and has a variable outer diameter.

5. The spinal implant according to claim 3, wherein the locking mechanism comprises a clamping portion disposed in the engagement tool, and is configured to clamp the engagement portion.

6. The spinal implant according to claim 1, wherein the second region comprises a screw hole.

7. The spinal implant according to claim 1, wherein the base comprises a rough surface portion, and the coating film covers at least a part of the rough surface portion.

8. The spinal implant according to claim 7, wherein
the rough surface portion is disposed in the first region, and a surface roughness of the rough surface portion is greater than a surface roughness of the second region.

9. The spinal implant according to claim 1, wherein the coating film is disposed directly on the base.

10. The spinal implant according to claim 1, further comprising: the first penetrating portion penetrating through the base in the first direction.

11. The spinal implant according to claim 10, further comprising:
the second penetrating portion penetrating through the base in the second direction that intersects the first direction.

12. The spinal implant according to claim 11, wherein the second penetrating portion comprises a plurality of through holes disposed separately from each other.

13. The spinal implant according to claim 1, wherein
antler surface of the base comprises two zones having different surface roughnesses.

14. The spinal implant according to claim 13, wherein the first region overlaps with a zone having a larger surface roughness among the two zones having different surface roughnesses.

15. A spinal implant comprising:
a base made of metal material and including a top face, a bottom face, and a side face; and
a coating film disposed on the base and comprising a calcium phosphate-based material and an antimicrobial agent, wherein
the coating film comprises a first region and a region having a smaller film thickness than a film thickness of the first region,
part of the first region is located in the side face, and
the region having a smaller film thickness is at least one of
(a) an inner surface of a first penetrating portion penetrating through the base in a first direction,
(b) an inner surface of a second penetrating portion penetrating through the base in a second direction that intersects the first direction, or
(c) a recessed portion provided on a rear face of the base.

16. The spinal implant according to claim 15, wherein
a surface of the base comprises two regions having different surface roughnesses, and the region having a smaller film thickness than the film thickness of the first region overlaps with a region having a smaller surface roughness among the two regions having different surface roughnesses.

* * * * *